(12) United States Patent
Carmignani et al.

(10) Patent No.: US 8,848,192 B2
(45) Date of Patent: Sep. 30, 2014

(54) EXTRACTIVE CONTINUOUS AMMONIA MONITORING SYSTEM

(71) Applicant: Fuel Tech, Inc., Warrenville, IL (US)

(72) Inventors: Paul G. Carmignani, Naperville, IL (US); John M. Boyle, Oak Park, IL (US); Scott M. Mayhew, North Aurora, IL (US)

(73) Assignee: Fuel Tech, Inc., Warrenville, IL (US)

( * ) Notice: Subject to any disclaimer, the term of this patent is extended or adjusted under 35 U.S.C. 154(b) by 0 days.

(21) Appl. No.: 13/890,623

(22) Filed: May 9, 2013

(65) Prior Publication Data

US 2013/0301053 A1 Nov. 14, 2013

Related U.S. Application Data

(60) Provisional application No. 61/645,330, filed on May 10, 2012.

(51) Int. Cl.

| | |
|---|---|
| *G01N 21/61* | (2006.01) |
| *G01N 21/35* | (2014.01) |
| *G01N 1/00* | (2006.01) |
| *G01N 1/22* | (2006.01) |
| *G01N 21/39* | (2006.01) |

(52) U.S. Cl.
CPC ............ *G01N 21/61* (2013.01); *G01N 21/3504* (2013.01); *G01N 1/00* (2013.01); *G01N 1/2247* (2013.01); *G01N 21/39* (2013.01)
USPC ........................................................ 356/437

(58) Field of Classification Search
CPC ... G01N 21/61; G01N 21/3504; G01N 21/39; G01N 1/00; G01N 1/2247

USPC .................................................. 356/432–444
See application file for complete search history.

(56) References Cited

U.S. PATENT DOCUMENTS

| | | | | |
|---|---|---|---|---|
| 5,429,805 | A * | 7/1995 | Uno et al. ........................ | 422/83 |
| 6,016,372 | A * | 1/2000 | Fein et al. ........................ | 385/12 |
| 6,114,700 | A * | 9/2000 | Blades .......................... | 250/343 |
| 8,143,581 | B2 * | 3/2012 | Wong ............................. | 250/345 |
| 8,237,927 | B1 * | 8/2012 | Reeve et al. ................... | 356/437 |
| 2006/0044562 | A1 * | 3/2006 | Hagene et al. ................ | 356/437 |
| 2008/0198027 | A1 * | 8/2008 | Bugge ........................... | 340/632 |
| 2011/0154806 | A1 * | 6/2011 | Hoyte et al. .................... | 60/276 |
| 2013/0166242 | A1 * | 6/2013 | Ido et al. ....................... | 702/104 |

* cited by examiner

*Primary Examiner* — Sang Nguyen
(74) *Attorney, Agent, or Firm* — Thaddius J. Carvis

(57) ABSTRACT

Disclosed are methods and apparatus for treating and analyzing a gas stream to determine the ammonia concentration. A gas stream is continuously monitored to determine the ammonia concentration by extracting gas samples from one or more locations and sending it to a tunable diode laser absorption spectroscopy instrument for analysis. By proper placement of sampling probes within a duct, depending on the particular flow patterns that have been determined by suitable modeling, e.g., computational fluid dynamics or cold flow modeling, the valves can be operated manually or by a controller to take samples at predetermined locations within the duct. This will enable taking samples from particular locations, samples representative of the entire cross section, or samples that are an average of a particular cross section. It will be possible by judicious placement of the probes and operation of the valves to map the concentrations of ammonia at a plurality of load settings and will permit continuous control.

4 Claims, 3 Drawing Sheets

EXTRACTIVE CONTINUOUS AMMONIA MONITORING SYSTEM

CROSS REFERENCE AND PRIORITY CLAIM

This application claims priority to U. S. Provisional Patent Application No. 61/645,330, filed May 10, 2012, the disclosure of which is incorporated herein by reference in its entirety.

FIELD OF THE INVENTION

The invention relates generally to continuously monitoring a gas stream to determine the ammonia concentration by extracting gas samples from one or more locations of an apparatus and analyzing the samples by tunable diode laser absorption spectroscopy.

BACKGROUND OF THE INVENTION

To assess the performance of a number of processes in which urea or ammonia are employed, it is often necessary to have the ability to determine how much ammonia is in a process or effluent stream. Traditionally, samples have been extracted an analyzed by chemiluminescent techniques, resulting in extended lag times between sample acquisition and analysis. These methods also lacked a desired precision at low concentrations because they relied upon assumptions to make the necessary calculations.

Recently, interest has turned to tunable diode laser (TDL) absorption spectroscopy. In a typical TDL installation, the transmitter and receiver are mounted directly to the ductwork. Since ammonia can convert to other compounds or be absorbed in ash at temperatures less than 500° F., the ideal installation location for a TDL is upstream of the air heater. Installations of this type are difficult for a variety of reasons. Access is frequently difficult due to limited space existing between the economizer or catalyst outlet and the air heater inlet. Walkways are frequently absent. TDL's rely upon the line of sight between the transmitter and receiver, with a longer distance aiding accuracy at low concentrations. However, as the distance increases, the required alignment of the device becomes more difficult. Thermal cycles can also affect this alignment. Ash loading degrades the signal and in high ash environments, a longer TDL path length may not be possible. Maintenance is frequently difficult due to the instruments installed, location and the challenges with access.

TDL's measure the ammonia concentration on a line of sight path between a transmitter and a receiver. If the gas flow is stratified and the ductwork is large, this ammonia concentration may not be indicative of the actual, overall ammonia concentration. For this reason, on larger units or units with multiple ducts, a typical TDL installation may require more than one transmitting and receiving unit.

Many commercial processes use extractive techniques to obtain samples of off-gas from the exhaust. The extracted gas is typically cooled and then analyzed using mass spectrometry or non-dispersive infrared absorption methods or chemical cells. However, the steps required to obtain a sample of the off-gas from extractive techniques can result in time delays in acquiring the data. By contrast, a process using real time sensors could obtain selective measurements of the off-gas constituents and provide adjustment of the inputs to a furnace on a continuous feedback loop. In one example of a continuous extractive analysis, WO 97/499979 to Frish, et al., describes a TDL system to monitor trace concentrations (e.g., on the order of one part per million) of ammonia in gases extracted from coal-fired utility boilers. The system includes a filter to remove particulates and a heater and temperature sensors that maintain the temperature of extracted gases. The device illustrated employs a Herriot cell to magnify TDL sensitivity in a small foot print, but this is not an ideal arrangement for use in obtaining accurate readings from a utility boiler where gas (and particulate) component compositions can vary across any given cross section.

Both selective noncatalytic $NO_x$ reduction (SNCR) and selective catalytic $NO_x$ reduction (SCR) processes used for controlling nitrogen oxides release from power plants and other combustors, employ ammonia either directly or indirectly as a $NO_x$-reducing reagent. It must be fed at the right concentrations and temperatures with regard to the $NO_x$ concentration to assure effective $NO_x$ control without excessive ammonia slip. There is always a delicate balance, and control systems must have accurate information to assure effective operation to comply with all regulations and guarantees as well as to avoid the practical problems of ammonium bisulfate production.

What is needed is a system designed to solve the difficulties of a typical TDL installation. A useful system would be capable of sampling gases over a broad array of locations through probes designed and operated to assure that extracted gas samples can be taken that are representative of actual operation conditions.

There is a present need for a process, apparatus and system that will enable the real-time analysis of ammonia concentration in a process or effluent stream.

SUMMARY OF THE INVENTION

The present invention provides processes, apparatus and systems for measurement of ammonia in a process or effluent stream.

In one aspect, a process is provided for continuously monitoring ammonia (or other gas species) in an apparatus utilizing flowing gas streams containing ammonia, comprising: providing at least one (preferably a plurality) of hollow sampling probe(s), each comprising a hollow tube having an internal passage defined by a tube wall having at least one opening through the tube wall and means for connecting the internal passage to an intake line; locating a plurality of said probes within the flowing gas stream positioned to permit communication between the internal passage in the tubes with the gas in the flowing gas stream; providing at least one valve for each hollow probe (in the case of a plurality) to control gas flow through a probe; creating a negative pressure differential between each internal passage of each probe and the flowing gas stream; directing flow of gases from the flowing gas stream through a sample path positioned between a transmitter and a receiver for a tunable diode laser; maintaining the temperature of the gases in the sample path at a predetermined value; directing a beam of light, tuned to a selected wave length (e.g., a narrow band), from the transmitter through the gas stream in the sample path to the receiver and generating a signal representative of the received signal; based on the signal calculating the concentration of ammonia in the gas stream; and, preferably, utilizing the concentration of ammonia as calculated to control one or more operational parameters.

In a preferred aspect the sample stream is redirected from the sample path to recombine with the flowing gas stream.

In another aspect, an apparatus is provided, comprising: at least one (preferably a plurality) of hollow sampling probe(s), each comprising a hollow tube having an internal passage defined by a tube wall having at least one opening through the tube wall and means for connecting the internal passage to an intake line; means for locating a plurality of said probes within the flowing gas stream positioned to permit communication between the internal passage in the tubes with the gas in the flowing gas stream; at least one valve for each hollow probe (in the case of a plurality) to control gas flow through a probe; means for creating a negative pressure differential between each internal passage of each probe and the flowing gas stream; means for directing flow of gases from the flowing gas stream through a sample path positioned between a transmitter and a receiver for a tunable diode laser; means for maintaining the temperature of the gases in the sample path at a predetermined value; means for directing a beam of light, tuned to a selected wave length, from the transmitter through the gas stream in the sample path to the receiver and generating a signal representative of the received signal; means for, based on the signal, calculating the concentration of ammonia in the gas stream; and, preferably, means for utilizing the concentration of ammonia as calculated to control one or more operational parameters.

In a further aspect, the invention provides a system employing the process and apparatus as disclosed.

Other and preferred aspects of the invention are described below.

DESCRIPTION OF THE DRAWINGS

The accompanying drawings, which are incorporated in and constitute a part of this description, illustrate presently preferred embodiments of the invention, and together with the detailed description of the preferred embodiments given below, serve to explain the principles of the invention. As shown throughout the drawings, like reference numerals designate like or corresponding parts.

DETAILED DESCRIPTION OF THE INVENTION

In describing the present invention, reference is made to the drawings, wherein a simplified, preferred embodiment is shown schematically. The drawings and the process and apparatus they represent will be described briefly below.

As noted above, a gas stream from a combustor has not been easily susceptible to continuous, accurate analysis for target species like ammonia by available equipment. The invention addresses this concern and provides a simple, reliable, low-cost solution.

Figure 1:
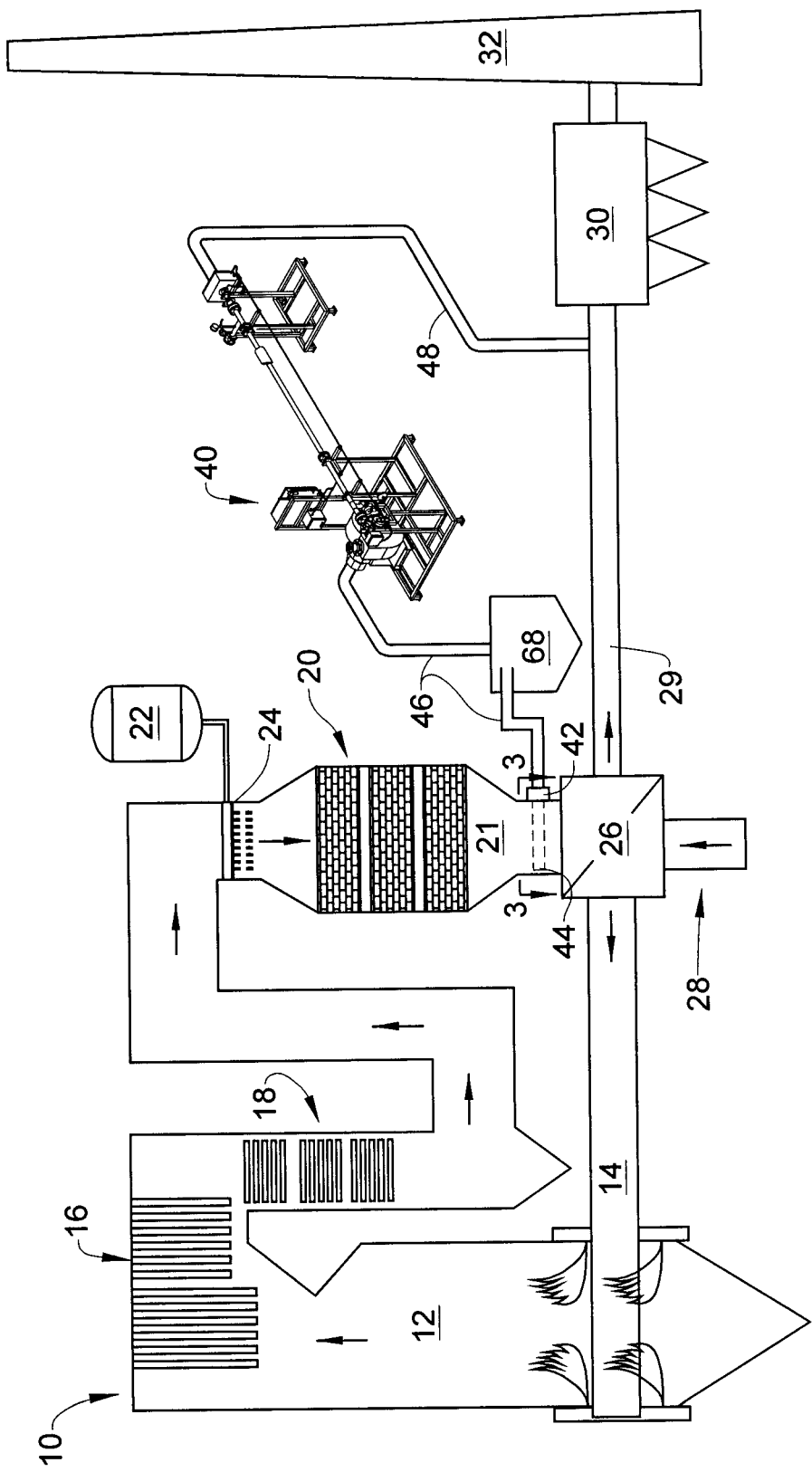
FIG. 1 is a schematic diagram of a combustion installation that takes advantage of the present invention employing a preferred embodiment of the process and system of the invention.

FIG. 1 is a schematic diagram of a combustion installation that takes advantage of the present invention to analyze a combustion effluent for ammonia slip, i.e., the ammonia that is left after SNCR or SCR treatment of exhaust gases by either injecting ammonia itself or another chemical used to provide active $NO_x$ reduction species.

The combustion installation includes a combustor 10 having burners that provide thermal heat in combustion zone 12 by burning fuel from a source not shown with air supplied by duct work 14. Hot combustion gases will pass through the furnace 10 in the direction indicated by the arrows, and the heat from combustion is transferred to heat exchangers 16 and 18 prior to passing into a selective catalytic reduction (SCR) reactor 20 wherein $NO_x$ created during combustion can be treated with a $NO_x$-reducing agent such as ammonia or gasified urea (including ammonia and HNCO) to convert the $NO_x$ to nitrogen and water. The $NO_x$-reducing agent is supplied, for example, by means of reagent storage tank 22 and injection grid 24. Alternatively, many installations will benefit from selective non catalytic reduction (SNCR) using urea alone or other $NO_x$-reducing agent at higher temperatures, e.g., as taught by Epperly, et al., in U.S. Pat. No. 5,057,293, without requiring the reactor 20.

Following SCR reactor 20, the combustion gases will flow through an air-to-air heat exchanger 26, which is used to preheat outside air supplied via duct 28 for delivery to the combustion zone 12 via line 14. The combustion gases leaving the heat exchanger 26 are cooled significantly by the time they are passed through duct work 29 to electrostatic precipitator (ESP) 30 wherein particulates are collected prior to passing the gases up stack 32. This is a highly-simplified version of actual industrial or utility combustors and effluent treatment processes, but illustrates a workable scheme.

Figure 3:
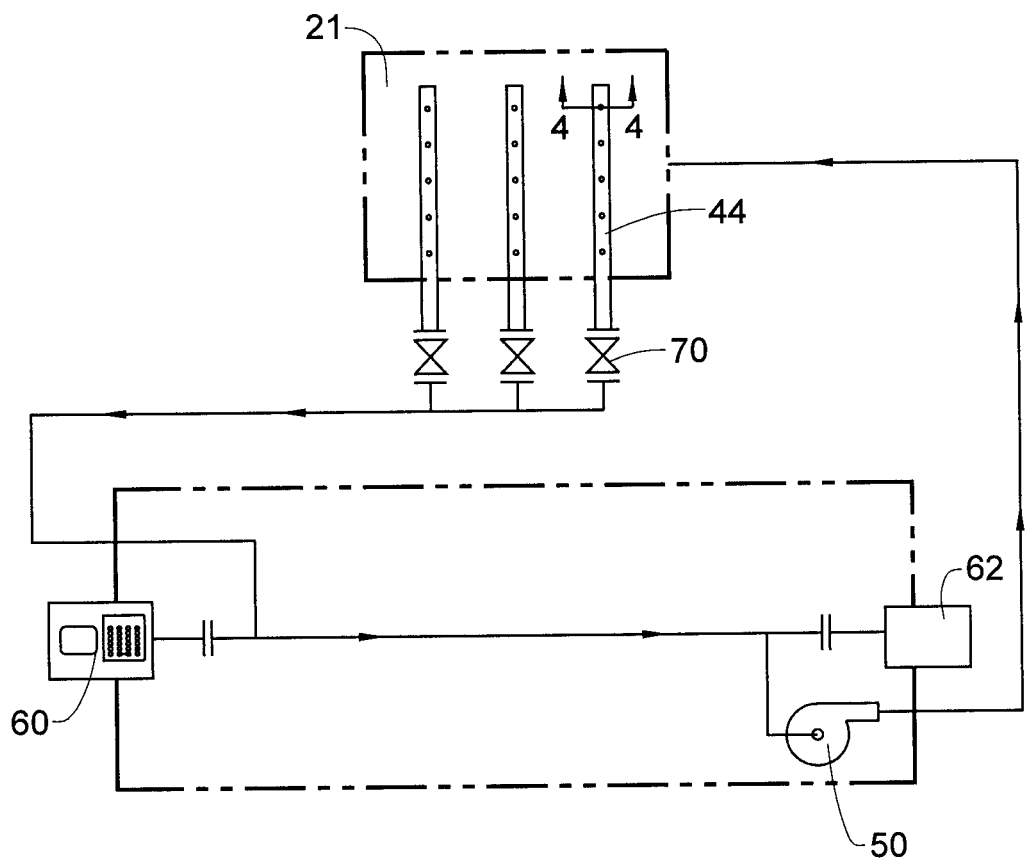
FIG. 3 is a cross section taken along line 3-3 in FIG. 1, showing a possible arrangement of sampling probes within a conduit containing a flowing gas stream of gases to be analyzed.

A tunable diode laser gas analyzer apparatus of the invention 40 is shown generally in FIG. 1 to include a support structure 42 for holding a plurality of hollow probes 44 (see FIG. 3 for a schematic arrangement). An intake line 46 is provided to direct a flow of gases to analyzer apparatus 40 from the flowing gas stream following the SCR reactor 20 to the probes 44.

Each of the probes 44 comprises a hollow tube having an internal passage 47 defined by a tube wall 45 having at least one opening 49 through the tube wall and means for connecting the internal passage to noted intake line 46. Once analyzed by passing through apparatus 40, the gases are returned via line 48 to the stream of exit gases, preferably just downstream of the sampling point (not shown), but can be later say in duct 29 (as illustrated). Lines 46 and 48 are shown schematically only and are preferably stainless steel pipe, which tends to be rigid. If suitable flexible tubing is available, it can be used.

Figure 2:
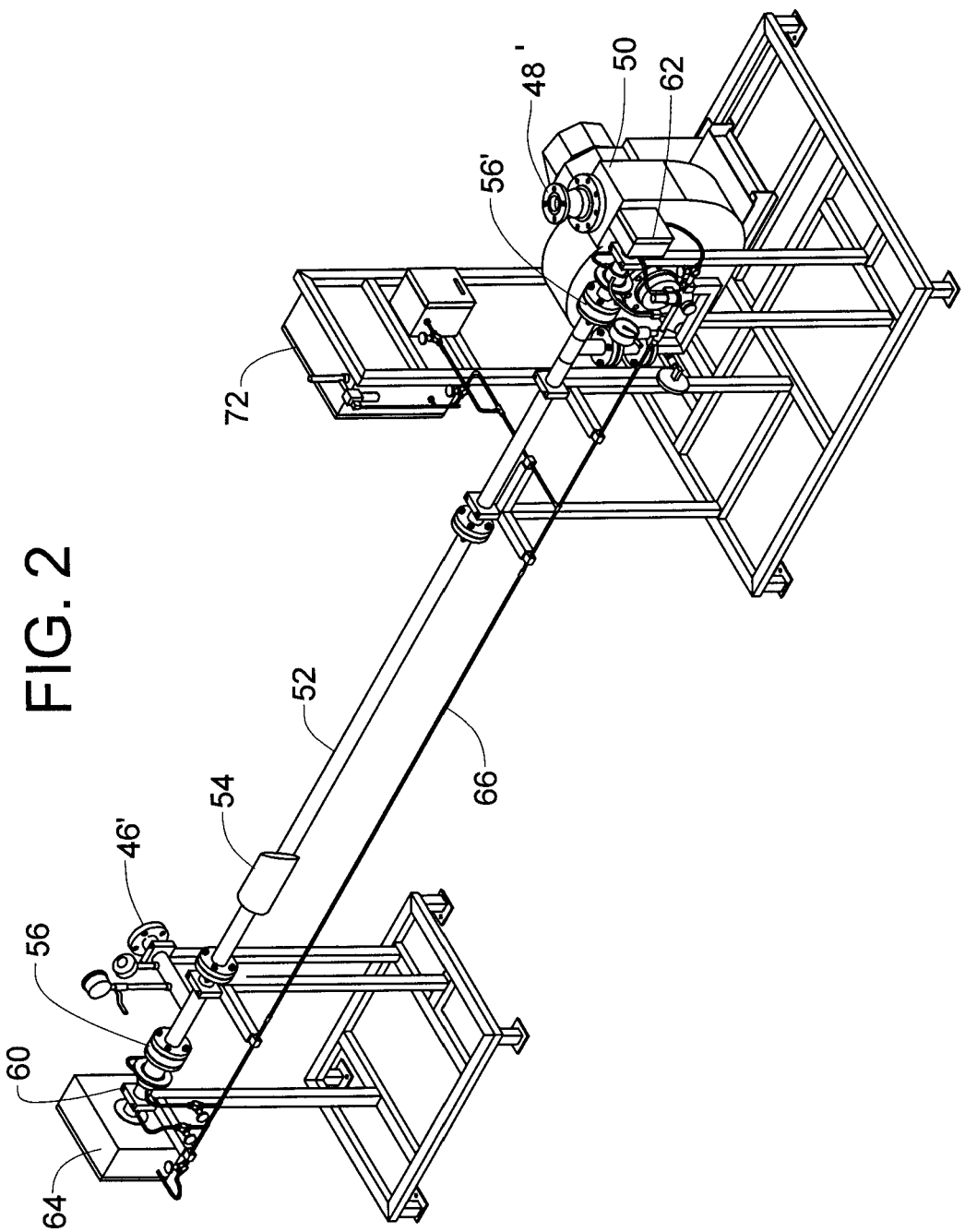
FIG. 2 is a schematic diagram showing greater detail of aspects of a system of the invention of the type shown in FIG. 1.

The invention enables simplified and real-time analysis of the stream for ammonia taken from a stream of gases flowing from the SCR unit 20 in duct 21, via intake line 46 to a suitable connection, such as intake flange 46' on apparatus 40, as best seen in FIG. 2. As will be apparent from the discussion of FIG. 3, the probes 44 can be fitted with valves and adjusted with the duct 21 to enable taking samples from particular locations, representative of the entire cross section, or an average of a particular cross section. A fan 50 is provided to pull the gases through apparatus 40 and return them to a suitable duct, say 29, via line 48 attached by means of a suitable connection, such as flange 48'. The gases to be analyzed are drawn into sample path 52, typically a stainless steel tube, by a negative pressure differential between each internal passage of each probe 44 and the flowing gas stream in duct 21. The sample path 52 is insulated, e.g., as shown partially at 54, to maintain the gas temperature and to avoid injury to operators. A preferred length of the sample path 52 is twelve feet but this may vary as requirements dictate, e.g., from about 3 to about 20 feet.

The sample path 52 has sight glasses 56 and 56' located on opposite ends, with 56 being at the transmitter end and 56' being at the receiver end to protect the transmitter 60 and the receiver 62 for a tunable diode laser from any contamination by the hot gases being directed through the sample path. The sight glasses physically separate the transmitter 60 and the receiver 62 from the interior of the sample path 52 while still permitting the transmitter 60 to direct a beam of light, tuned to a selected wave length, and for the receiver 62 to receive it for analysis by logic and computation unit 64. Electrical power to the transmitter and control signals to and from the logic and computation unit 64 can be supplied via electrical lines shown generally as 66. A supply of cooling air, not shown, is preferably provided to each of the transmitter 60 and the receiver 62 units to maintain a safe operating temperature.

The temperature of the gases in the sample path 52 is easily maintained at a predetermined value, e.g., at least about 450° F., and preferably within the range of from 500° to 600° F., without any additional heat by maintaining a suitably high flow rate through the path 52. The sample path can be heated by heaters, not shown, that can be embedded in insulation 54, if necessary. It is an advantage of the invention is that the high flow rate of hot gases makes heating unnecessary except in anomalous situations. In the exemplary situation of a two inch diameter sample chamber path 52, which is twelve feet long, a flow rate of 120 scfm (e.g., from 20 to 300 scfm) provides a complete exchange of gases about eight times per second. The entire system residence time will typically be less than a second. This assures the gases will not cool substantially. In a target system residence time will be between 0.2 and 5 seconds, e.g., about 1 second, preferably and that the target measurement volume residence time is within this range where temperatures can be maintained and extractive effectiveness retained, and preferably between 0.05 and 0.5 seconds. The high flow rate also can eliminate the need for a filter to remove ash in embodiments where the ash is never given the opportunity to collect. In others, the use of a cyclone 68, receiving gas from line 46 and discharging it to the analyzer apparatus 40, can effectively handle significant ash loadings.

The details of the wavelengths of light, electrical and temperature requirements for the particular tunable diode laser selected, will all be available from the manufacturer. We presently prefer Yokogawa TDLS200 analyzer, but there is no criticality in this selection. The analyzer is capable of directing a beam of light, tuned to a selected wave length, typically tuned within a narrow band (e.g., a resolution of less than 0.02 nm) of wavelengths, from the transmitter 60 through the gas stream in the sample path 52 to the receiver 62 and generating a signal representative of the received signal. Based on the signal, the logic and computation unit 64 is capable of calculating the concentration of ammonia in the gas stream, and will do so. Based on this signal representative of the ammonia concentration, a process controller, e.g., for the SCR reactor and ammonia supply will control one or more operational parameters.

Figure 4:
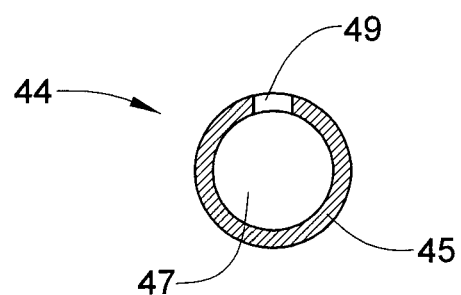
FIG. 4 is a cross section of a sampling probe taken along line 4-4 in FIG. 3.

Detail and arrangement of the probes 44 are illustrated schematically in FIG. 3, with FIG. 4 showing a cross section of one probe 44 taken along line 4-4 in FIG. 3. It can be seen that each probe 44 comprises a hollow tube having an internal passage defined by a tube wall having at least one opening through the tube wall and means for connecting the internal passage to an intake line. FIG. 4 shows tube 44 having a central opening 45 with a hole 47 therethrough. As seen in FIG. 3, there can be a plurality of holes. Means, which may be simple brackets (represented by the outer dotted lines at 44 in FIG. 1, are provided to enable locating a plurality of the probes within the flowing gas stream in duct 21 and to position them effectively to permit communication between the internal passage 47 in the tubes with the gas in the flowing gas stream in duct 21. At least one valve 70 is provided for each hollow probe to control gas flow through a probe. By proper placement of the probes within duct 21, depending on the particular flow patterns that have been determined by suitable modeling, e.g., computational fluid dynamics or cold flow modeling, the valves 70 can be operated manually or by a controller to take samples at predetermined locations within the duct 21. This will enable taking samples from particular locations, samples representative of the entire cross section, or samples that are an average of a particular cross section. It will be possible by judicious placement of the probes 44 and operation of the valves 70 to map the concentrations of ammonia at a plurality of load settings and will permit continuous control. The invention provides the ability to test at various locations along the flue gas path as boiler load changes without the need to install transmitter and receiver pairs at each location to be tested. While lacking the full mapping capability, it will be possible to install the above apparatus with a single probe, without any valve and still take advantages of some aspects of the invention.

Systems employing the process and apparatus combine the disclosed features and incorporate details as necessary for a wide variety of industrial applications.

The above description is for the purpose of teaching the person of ordinary skill in the art how to practice the invention. It is not intended to detail all of those obvious modifications and variations, which will become apparent to the skilled worker upon reading the description. It is intended, however, that all such obvious modifications and variations be included within the scope of the invention which is defined by the following claims. The claims are meant to cover the claimed components and steps in any sequence which is effective to meet the objectives there intended, unless the context specifically indicates the contrary.

What is claimed is:

1. A process for continuously monitoring ammonia (or other gas species) in an apparatus utilizing flowing gas streams containing ammonia, comprising:
   a. providing at least one hollow probe, each comprising a hollow tube having an internal passage defined by a tube wall having at least one opening through the tube wall and means for connecting the internal passage to an intake line;
   b. locating at least one of said probes within the flowing gas stream positioned to permit communication between the internal passage in the tubes with the gas in the flowing gas stream;
   c. creating a negative pressure differential between each internal passage of each probe and the flowing gas stream;
   d. directing flow of gases from the flowing gas stream through a sample path positioned between a transmitter and a receiver for a tunable diode laser;
   e. maintaining the temperature of the gases in the sample path at a predetermined value;
   f. directing a beam of light, tuned to a selected wave length, from the transmitter through the gas stream in the sample path to the receiver and generating a signal representative of the received signal;
   g. based on the signal, using a logic and computation unit to calculate the concentration of ammonia in the gas stream.

2. A process according to claim 1, further including utilizing the concentration of ammonia as calculated to control one or more operational parameters.

3. A process according to claim 1 wherein the sample stream is redirected from the sample path to recombine with the flowing gas stream.

4. A process according to claim 1 wherein a plurality of probes are provided and providing at least one valve for each hollow probe to control gas flow through a probe.

* * * * *